United States Patent [19]

King

[11] Patent Number: 5,245,032

[45] Date of Patent: Sep. 14, 1993

[54] CATALYTIC PROCESSES FOR THE PREPARATION OF N,N,N-TRISUBSTITUTED NITROGEN-CONTAINING COMPOUNDS

[75] Inventor: Stephen W. King, Scott Depot, W. Va.

[73] Assignee: Union Carbide Chemicals & Plastics Technology Corporation, Danbury, Conn.

[21] Appl. No.: 585,561

[22] Filed: Sep. 20, 1990

[51] Int. Cl.$^5$ .............. C07D 295/02; C07D 295/03; C07D 241/12; B01J 25/00

[52] U.S. Cl. .................. 544/162; 544/106; 544/177; 544/178; 544/358; 544/401; 544/402; 544/404; 548/215; 564/58; 564/60; 564/61; 564/463; 564/503; 564/505

[58] Field of Search .............. 544/358, 106, 162, 177, 544/178, 401, 402, 404; 542/215; 564/58, 60, 61, 403, 503, 505

[56] References Cited

U.S. PATENT DOCUMENTS

| | | | |
|---|---|---|---|
| 3,087,928 | 4/1963 | Godfrey | 544/358 |
| 4,667,045 | 5/1987 | Briggs et al. | 544/358 |
| 4,967,018 | 10/1990 | Soo et al. | 544/358 |

FOREIGN PATENT DOCUMENTS

| | | | |
|---|---|---|---|
| 3836781 | 10/1988 | Fed. Rep. of Germany | 544/358 |
| 1238478 | 11/1967 | United Kingdom | 544/358 |

OTHER PUBLICATIONS

March J., Advanced Organic Chemistry: Reactions, Mechanisms, and Structure, 1968, pp. 435-436, 477-480 and 878-879.

Dow Chemical U.S.A., Experimental Ethylene Carbonate XAS-1666.00L Product Bulletin (1982), pp. 5-7.

Texaco Chemical Company, TEXACAR ® Ethylene and Propylene Carbonates Product Bulletin (1987), pp. 22-23.

Trotta, F. et al., J. Org. Chem., 1987, 52, pp. 1300-1304.

Enichem Synthesis SpA; Dimethyl Carbonate Product Bulletin, pp. 10-13, Jul. 1987.

Primary Examiner—Floyd D. Higel
Attorney, Agent, or Firm—R. M. Allen

[57] ABSTRACT

A process for preparing N,N,N-trisubstituted nitrogen-containing compounds which comprises contacting a carboxylated N,N,N-trisubstituted nitrogen-containing compound with a mixed metal oxide catalyst under conditions effective to produce the N,N,N-trisubstituted nitrogen-containing compound.

50 Claims, No Drawings

CATALYTIC PROCESSES FOR THE PREPARATION OF N,N,N-TRISUBSTITUTED NITROGEN-CONTAINING COMPOUNDS

RELATED APPLICATIONS

The following are related, commonly assigned applications, filed on an even date herewith:
U.S. patent application Ser. No. 07/585,560; U.S. patent application Ser. No. 07/585,455; U.S. patent application Ser. No. 07/585,563; U.S. patent application Ser. No. 07/585,564; U.S. patent application Ser. No. 07/585,559; U.S. patent application Ser. No. 07/585,456; U.S. patent application Ser. No. 07/585,565; U.S. patent application Ser. No. 07/585,555(now U.S. Pat. No. 5,104,487) ; and U.S. patent application Ser. No. 07/585,556; all of which are incorporated herein by reference.

BRIEF SUMMARY OF THE INVENTION

Technical Field

This invention relates to a process for preparing N,N,N-trisubstituted nitrogen-containing compounds which comprises contacting a carboxylated N,N,N-trisubstituted nitrogen-containing compound with a mixed metal oxide catalyst under conditions effective to produce the N,N,N-trisubstituted nitrogen-containing compound.

Background of the Invention

Decarboxylation, that is, elimination of the —COOH group as $CO_2$, is a known process. March, J., Advanced Organic Chemistry: Reactions, Mechanisms, and Structure, 1968, pp. 435–436, 477–480 and 878–879, describes various decarboxylation reactions. At pages 435–436, it is stated that aromatic acids can be decarboxylated by heating with copper and quinoline. At pages 477–480, it is stated that aliphatic acids which undergo successful decarboxylation have certain functional groups or double or triple bonds in the alpha or beta positions such as malonic acids, alpha-cyano acids, alpha-nitro acids, alpha-aryl acids, alpha-keto acids, alpha-trihalo acids, beta-keto acids, beta,gamma-olefinic acids and the like. At pages 878–879, oxidative decarboxylation is described in which lead tetraacetate cleaves carboxyl groups, replacing them with acetoxy groups, which may be hydrolyzed to hydroxyl groups. It is stated that compounds containing carboxyl groups on adjacent carbons (succinic acid derivatives) can be bisdecarboxylated with lead tetraacetate. It is also stated that compounds containing geminal carboxyl groups (malonic acid derivatives) can be bisdecarboxylated with lead tetraacetate, gem-diacetates (acylals) being produced, which are hydrolyzable to ketones.

Enichem Synthesis SpA, Dimethyl Carbonate Product Bulletin, pp. 10–13, discloses the reaction of aromatic amines with dimethyl carbonate to give N-methyl and N,N'-dimethyl aromatic amines. It is stated that the reaction is carried out under the same conditions as used for the methylation of phenols. The reaction of phenols with dimethyl carbonate is carried out in the presence of a basic catalyst such as NaOH, $Na_2CO_3$, $NaOCH_3$, tertiary amines and heterocyclic nitrogenous compounds. Reaction temperatures of at least 140° C. are required. It is stated that the speed of reaction can be accelerated with catalytic quantities of organic and inorganic halides. At page 12, it is stated that dimethyl carbonate reacts with amines (aliphatic or aromatic, Primary or secondary) to Produce carbamates and ureas. At page 13, it is stated that aminoalcohols can react with dimethyl carbonate in the presence of sodium or potassium alkoxides to yield 2-oxazolidinones.

Dow Chemical U.S.A., Experimental Ethylene Carbonate XAS-1666.00L Product Bulletin (1982), pp. 5–7, discloses that aromatic amines can be reacted with ethylene carbonate to form N-(2-hydroxyethyl) derivatives. It is stated that with primary amines such as aniline, a mixture of mono- and di-substituted derivatives can be prepared. It is also stated that carbamates and imidazolidinones can be Produced through the reaction of ethylene carbonate with aliphatic mono- and di-amines.

Texaco Chemical Company, TEXACAR ® Ethylene and Propylene Carbonates Product Bulletin (1987), pp. 22–23, describes the reaction of ethylene carbonate and propylene carbonate with primary and secondary aliphatic amines at low temperatures to Yield carbamates. It is stated that ethylene carbonate and propylene carbonate can react with amines to give the corresponding hydroxyethyl and hydroxypropyl derivatives.

Trotta, F. et al., J. Org. Chem., 1987, 52, pp. 1300–1304, relates to selective mono-N-alkylation of aromatic amines by dialkyl carbonate under gas-liquid phase-transfer catalysis conditions (continuous flow process). The catalyst is a polyethylene glycol in the presence of a base ($K_2CO_3$).

DISCLOSURE OF THE INVENTION

This invention relates to a process for preparing N,N,N-trisubstituted nitrogen-containing compounds which comprises contacting a carboxylated N,N,N-trisubstituted nitrogen-containing compound with a mixed metal oxide catalyst under conditions effective to produce the N,N,N-trisubstituted nitrogen-containing compound.

This invention also relates to a process for preparing N,N,N-trisubstituted nitrogen-containing compounds which comprises contacting a N,N-disubstituted nitrogen-containing compound with a $CO_2$ synthon in the presence of a mixed metal oxide catalyst under conditions effective to produce the N,N,N-trisubstituted nitrogen-containing compound.

This invention further relates to a process for preparing N,N,N-trisubstituted nitrogen-containing compounds which comprises (i) contacting a N,N-disubstituted nitrogen-containing compound with a $CO_2$ synthon under conditions effective to produce a carboxylated N,N,N-trisubstituted nitrogen-containing compound, and (ii) contacting the carboxylated N,N,N-trisubstituted nitrogen-containing compound with a mixed metal oxide catalyst under conditions effective to produce the N,N,N-trisubstituted nitrogen-containing compound.

The N,N,N-trisubstituted nitrogen-containing compounds produced in accordance with the processes of this invention are useful for a wide variety of applications such as solvents, liquid absorbents, polyurethane catalysts, acid gas scrubbing agents and the like. Preferred N,N,N-trisubstituted nitrogen-containing compounds produced by the processes of this invention include nonaromatic cyclic nitrogen-containing compounds having a ring tertiary-substituted nitrogen such as N- and N, N'-substituted piperazines, N-substituted morpholines, N- and N,N'-substituted 2-imidazolidinones or ethylene ureas, and N-substituted 2-oxazolidinones.

For purposes of this invention, the chemical elements are identified in accordance with the Periodic Table of the Elements, CAS version, Handbook of Chemistry and Physics, 67th Ed., 1986–87, inside cover. Also, for purposes of this invention, Group IIIB metal oxides embraces the lanthanides and actinides. As used herein, the term "oxide" embraces oxides, hydroxides and/or mixtures thereof. Also, as used herein, the term "$CO_2$ synthon" embraces $SO_2$ synthons such as sulfurous acids and sulfurous acid esters.

DETAILED DESCRIPTION

As indicated above, this invention relates to a process for preparing N,N,N-trisubstituted nitrogen-containing compounds which comprises contacting a carboxylated N,N,N-trisubstituted nitrogen-containing compound with a mixed metal oxide catalyst under conditions effective to produce the N,N,N-trisubstituted nitrogen-containing compound.

As also indicated above, this invention relates to a process for preparing N,N,N-trisubstituted nitrogen-containing compounds which comprises contacting a N,N-disubstituted nitrogen-containing compound with a $CO_2$ synthon in the presence of a mixed metal oxide catalyst under conditions effective to produce the N,N,N-trisubstituted nitrogen-containing compound.

As further indicated above, this invention relates to a process for preparing N,N,N-trisubstituted nitrogen-containing compounds which comprises (i) contacting a N,N-disubstituted nitrogen-containing compound with a $CO_2$ synthon under conditions effective to produce a carboxylated N,N,N-trisubstituted nitrogen-containing compound, and (ii) contacting the carboxylated N,N,N-trisubstituted nitrogen-containing compound with a mixed metal oxide catalyst under conditions effective to produce the N,N,N-trisubstituted nitrogen-containing compound.

When a N,N-disubstituted nitrogen-containing compound and $CO_2$ synthon are employed as starting materials, it is believed that a transesterification reaction followed by a decarboxylation reaction occurs to provide the desired N,N,N-trisubstituted nitrogen-containing compound product. The exact reaction mechanism is not fully appreciated but what is appreciated is that a N,N-disubstituted nitrogen-containing starting material and $CO_2$ synthon starting material can be contacted in the presence of a mixed metal oxide catalyst under conditions described herein to provide a N,N,N-trisubstituted nitrogen-containing compound product. It is also appreciated that a carboxylated N,N,N-trisubstituted nitrogen-containing compound can be contacted with a mixed metal oxide catalyst under conditions described herein to provide a N,N,N-trisubstituted nitrogen-containing compound product.

Step (i) of certain processes of this invention can in general be referred to as a transesterification reaction. Any suitable transesterification catalyst can be employed in step (i). Such transesterification catalysts are known and include, for example, basic metal oxides, alkoxides and other basic metal salts such as potassium carbonate, sodium titanate and the like. Other suitable transesterification catalysts include, for example, Bronsted acids such as sulfuric acid and Lewis acids such as aluminum triisopropoxide. As discussed hereinafter in regard to the decarboxylation catalyst, the transesterification catalyst employed in this invention likewise may also contain support(s), binding agent(s) or other additives to stabilize or otherwise help in the manufacture of the catalyst. Both homogeneous and heterogeneous catalysts can be employed in the step (i) reaction. The amount of transesterification catalyst used in step (i) is dependent on the particular catalyst employed and can range from about 0.01 weight percent or less to about 10 weight percent or greater of the total weight of the starting materials.

Suitable N,N-disubstituted nitrogen-containing compound starting materials which can be employed in the step (i) transesterification reaction include any permissible substituted or unsubstituted N,N-disubstituted nitrogen-containing compound(s) such as those embraced by the formula RNHR wherein R is the same or different and is the residue of an organic compound. It is understood that the R substituents together can complete a heterocycloalkyl ring which can be substituted or unsubstituted. Preferred N,N-disubstituted nitrogen-containing compound starting materials include N,N-disubstituted acyclic and cyclic compounds such as diethanolamine, piperazine, morpholine, 2-oxazolidinone and 2-imidazolidinone. Illustrative N,N-disubstituted nitrogen-containing compound starting materials useful in this invention include, for example, diethanolamine, piperazine, 1-hydroxyethypiperazine, morpholine, piperidine, pyrrolidine, 2-oxazolidi-none, 2-imidazolidinone, diisopropylamine, dimethylamine, diethylamine and the like. The molar ratio of N,N-disubstituted nitrogen-containing compound to $CO_2$ synthon is not narrowly critical and can range from about 0.05:1 or less to about 50:1 or greater, preferably from about 0.1:1 to about 10:1.

Suitable $CO_2$ synthon starting materials which can be employed in the step (i) transesterification reaction include any permissible substituted or unsubstituted carboxyl-containing compound(s) or carbonyl-containing compound(s) which are capable of reacting with a N,N-disubstituted nitrogen-containing compound under the process conditions described herein, such as those embraced by the formulae $R_1C(O)R_2$ or $R_1S(O)R_2$ wherein $R_1$ is hydrogen, halogen, amino, hydroxyl or the residue of an organic compound, and $R_2$ is amino, hydroxyl or the residue of an organic compound. Illustrative $CO_2$ synthons include, for example, substituted and unsubstituted carbonates, chlorocarbonates, carbonic acids, carbamates, carbamic acids, oxalates, 2-oxazolidinones, ureas, esters, phosgene, chloroformates, carbon dioxide, orthocarboxylates, sulfurous acids, sulfurous acid esters and the like. For purposes of this invention, carbon monoxide is also considered a $CO_2$ synthon for appropriate oxidative carbonylation reactions. Preferred $CO_2$ synthons include, for example, diethyl carbonate, ethylene carbonate, dimethyl carbonate, methyl chlorocarbonate, ethyl chlorocarbonate, 2-oxazolidinone, ethylene sulfite and the like. The use of $CO_2$ synthons prepared in situ such as the reaction of ethylene carbonate and monoethanolamine to give 2-oxazolidinone is encompassed within the scope of this invention.

As indicated above, $R_1$ and $R_2$ can be the residue of an organic compound. Illustrative residues of organic compounds include, for example, alkyl, aryl, alkylamino, arylamino, alkyloxy, aryloxy, cycloalkyl, heterocycloalkyl, cycloalkyloxy, heterocycloalkyloxy, alkyloxycarbonyl, aryloxycarbonyl, cycloalkyloxycarbonyl, heterocycloalkyloxycarbonyl, hydroxycarbonyl and the like. Additionally, for purposes of defining the $CO_2$ synthon by the formulae above, the $R_1$ and $R_2$ substituents together can complete a cycloalkyl ring or a heterocycloalkyl ring which can be substituted or unsubstituted. The $R_1C(O)R_2$ formula is also contemplated to embrace carbon dioxide and carbon monoxide.

The step (i) transesterification reaction can be conducted over a wide range of pressures ranging from atmospheric or subatmospheric pressures to superatmospheric pressures. However, the use of very high pressures has not been observed to confer any significant advantages but increases equipment costs. Further, it is preferable to conduct the step (i) reaction at reduced pressures of from about 1 mm Hg to less than about 760 mm Hg. The step (i) transesterification reaction is preferably effected in the liquid or vapor states or mixtures thereof.

The temperature of the step (i) transesterification reaction may be as low as about ambient temperature to about 300° C. Preferably, the reaction temperature ranges from about 50° C. to about 200° C., and most preferably from about 60° C. to about 120° C.

Suitable carboxylated N,N,N-trisubstituted nitrogen-containing compounds prepared by the step (i) transesterification reaction include any permissible carboxylated N,N,N-trisubstituted nitrogen-containing compounds which are capable of eliminating carbon dioxide under the process conditions described herein, such as those embraced by the formulae $RN(C(O)OR_1)R$ or $RN(C(O)OR_2)R$ wherein R, $R_1$ and $R_2$ are as defined above. It is understood that the R substituents together can complete a heterocycloalkyl ring which can be substituted or unsubstituted. Illustrative carboxylated N,N,N-trisubstituted nitrogen-containing compounds include, for example, methyl diethanolamine carbamate, methyl 1-piperazine carboxylate, ethyl 1-Piperazine carboxylate, methyl 4-methyl-1-piperazine carboxylate, 2-(2-methoxyethoxy)ethyl N,N-dimethyl carbamate, 2-(2-methoxyethoxy)ethyl methyl carbamate, methyl 2-oxazolidinone carboxylate, ethyl 2-oxazolidinone carboxylate, methyl 2-imidazolidinone carboxylate, ethyl 2-imidazolidinone carboxylate, methyl 1-morpholine carboxylate, ethyl 1-morpholine carboxylate and the like. The amount of carboxylated N,N,N-tri-substituted nitrogen-containing compound(s) employed in step (ii) is dependent on the amount of mixed metal oxide catalyst employed.

The carboxylated N,N,N-trisubstituted nitrogen-containing compounds prepared by the step (i) transesterification reaction may undergo one or more transesterifications prior to the step (ii) decarboxylation reaction. For example, a hydroxyl-containing compound may be reacted with the originally prepared carboxylated N,N,N-tri-substituted nitrogen-containing compound under conditions effective to prepare a different carboxylated N,N,N-trisubstituted nitrogen-containing compound. Suitable hydroxyl-containing compounds include those embraced by the formula $R_3OH$ wherein $R_3$ is the residue of an organic compound. This invention is not intended to be limited in any manner by the step (i) transesterification reaction.

Step (ii) of certain processes of this invention can in general be referred to as a decarboxylation reaction. Suitable decarboxylation catalysts which can be employed in step (ii) include two or more metal oxides. A magnesium:aluminum mixed metal oxide is a preferred mixed metal oxide catalyst as more fully described below. Both homogeneous and heterogeneous catalysts can be employed in the step (ii) reaction. The amount of decarboxylation catalyst used in step (ii) is not narrowly critical and is dependent on whether step (ii) is conducted batchwise or continuously. If batchwise, the catalyst employed can range from about 0.01 weight percent or less to about 10 weight percent or greater of the total weight of the starting materials. If continuously, generally a fixed bed is employed.

Suitable decarboxylation catalysts for use in the processes of this invention comprise mixed metal oxides containing two or more metal oxides. Illustrative of such mixed metal oxides include, for example, two or more of the following: Group IA metal oxides, Group IIA metal oxides, Group IIIB metal oxides (including lanthanides and actinides), Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides. Certain of these metal oxide(s) may also be used as transesterification catalysts in accordance with this invention such as Group IIA and/or IIIA metal oxides. Preferred mixed metal oxides are amphoteric or basic. Preferred mixed metal oxides which may be utilized as decarboxylation catalysts include, for example, two or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

Group IIA metal oxides such as magnesium oxide and calcium oxide and Group IIIA metal oxides such as aluminum oxide and gallium oxide are Preferred mixed metal oxides for use in this invention. For mixed metal oxides in which at least one of the metals is magnesium, suitable metals in association with magnesium may include, for example, one or more of the following: Group IIIA metals such as boron, aluminum, gallium and indium, Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IVA metals such as silicon, germanium, tin and lead, Group VA metals such as arsenic, antimony and bismuth, and Group IVB metals such as zirconium and hafnium. For mixed metal oxides in which at least one of the metals is calcium, suitable metals in association with calcium may include, for example, one or more of the following: Group IIIA metals such as boron, aluminum, gallium and indium, Group IVA metals such as silicon, germanium, tin and lead, Group VB metals such as niobium and tantalum, and Group VIB metals such as chromium, molybdenum and tungsten.

Illustrative of mixed metal oxides which may be used as decarboxylation catalysts include, for example, $MgO-Al_2O_3$, $MgO-SiO_2$, $MgO-CdO$, $MgO-Bi_2O_3$, $MgO-Sb_2O_5$, $MgO-SnO_2$, $MgO-ZrO_2$, $MgO-BeO$, $MgO-TiO_2$, $MgO-CaO$, $MgO-SrO$, $MgO-ZnO$, $MgO-Ga_2O_3$, $MgO-Y_2O_3$, $MgO-La_2O_3$, $MgO-MoO_3$, $MgO-Mn_2O_3$, $MgO-Fe_2O_3$, $MgO-Co_3O_4$, $MgO-WO_3$, $MgO-V_2O_5$, $MgO-Cr_2O_3$, $MgO-ThO_2$, $MgO-Na_2O$, $MgO-BaO$, $MgO-CaO$, $MgO-HfO_2$, $MgO-Li_2O$, $MgO-Nb_2O_5$, $MgO-Ta_2O_5$, $MgO-Gd_2O_3$, $MgO-Lu_{2O3}$, $MgO-Yb_2O_3$, $MgO-CeO_2$, $MgO-Sc_2O_3$, $MgO-PbO$, $MgO-$ NiO, MgO-CuO, MgO-CoO, MgO-$B_2O_3$, CaO-$SiO_2$, CaO-$Al_2O_3$, CaO-SnO, CaO-PbO, CaO-$Nb_2O_5$, CaO-$Ta_2O_5$, CaO-$Cr_2O_3$, CaO-$MoO_3$, CaO-$WO_3$, CaO-$TiO_2$, CaO-$HfO_2$, MgO-$SiO_2$-$Al_2O_3$, MgO-$SiO_2$-ZnO, MgO-$SiO_2$-$ZrO_2$, MgO-$SiO_2$-CuO, MgO-$SiO_2$-CaO, MgO-$SiO_2$-$Fe_2O_3$, MgO-$SiO_2$-$B_2O_3$, MgO-$SiO_2$-$WO_3$, MgO-$SiO_2$-$Na_2O$, MgO-$SiO_2$-$Ga_2O_3$, MgO-$SiO_2$-$La_2O_3$, MgO-$SiO_2$-$Nb_2O_5$, MgO-$SiO_2$-$Mn_2O_3$, MgO-$SiO_2$-$Co_3O_4$, MgO-$SiO_2$-NiO, MgO-$SiO_2$-PbO, MgO-$SiO_2$-$Bi_2O_3$, MgO-$Al_2O_3$-ZnO, MgO-$Al_2O_3$-$ZrO_2$, MgO-$Al_2O_3$-$Fe_2O_3$, MgO-$Al_2O_3$-$WO_3$, MgO-$Al_2O_3$-$La_2O_3$, MgO-$Al_{23}$-$Co_3O_4$, CaO-$SiO_2$-$Al_2O_3$, CaO-$SiO_2$-SnO, CaO-$SiO_2$-$Nb_2O_5$, CaO-$SiO_2$-$WO_3$, CaO-$SiO_2$-$TiO_2$, CaO-$SiO_2$-$MoO_3$, CaO-$SiO_2$-$HfO_2$, CaO-$SiO_2$-$Ta_2O_5$, CaO-$Al_2O_3$-$SiO_2$, CaO-$Al_2O_3$-PbO, CaO-$Al_2O_3$-$Nb_2O_5$, CaO-$Al_2O_3$-$WO_3$, CaO-$Al_2O_3$-$TiO_2$, CaO-$Al_2O_3$-$MoO_3$, CaO-$HfO_2$-$Al_2O_3$, CaO-$HfO_2$-$TiO_2$, and the like. Other suitable mixed metal oxides embraced within the scope of this invention are disclosed by Tanabe et al , Bulletin of the Chemical Society of Japan, Vol. 47(5), pp. 1064–1066 (1974).

The mixed metal oxides described herein which can be used as decarboxylation catalysts may contribute to product selectivity and/or catalytic activity of the reaction and/or stability of the catalyst. As discussed hereinafter, the decarboxylation catalyst employed in this invention may also contain support(s), binding agent(s) or other additives to stabilize or otherwise help in the manufacture of the catalyst.

The decarboxylation catalysts which comprise two or more metal oxides may be prepared in a wide variety of ways. For example, the two or more metal oxides can be provided from metal salts which can either be heated or precipitated to form the mixed metal oxides. Also, two or more metal oxides may be provided as a partial condensate on a support, such as a silica or alpha, beta or gamma alumina, silicon carbide, and the like, and then condensed by heating to effect polymerization to the desired oxide form. The two or more metal oxides may be condensed from hydrolyzable monomers to the desired oxides, indeed, to form oxide powders which can thereafter be compressed in the Presence of a condensation catalyst to form pellets and larger structures of the mixed metal oxide decarboxylation catalyst. A blend of the powders and condensation catalyst can be made into a shapeable paste which can be extruded and cut into pellets according to conventional procedures. The extrudate may thereafter be fired to cure the condensation catalyst and fix the structure. The cut extrudate may be blended with a support material such as those characterized above, and the blend fired to fuse the mixed metal oxide catalyst to the support.

In an embodiment of this invention, a magnesium salt, e.g., magnesium nitrate, and an aluminum salt, e.g., aluminum nitrate, are precipitated using ammonium hydroxide. The material is then washed with deionized water and calcined at a temperature of from about 350° C. to about 450° C to afford the desired magnesium:aluminum mixed metal oxide catalyst.

In another embodiment, a magnesium oxide, e.g., magnesium carbonate hydroxide pentahydrate, and an aluminum oxide, e.g., aluminum hydroxide hydrate, are added to deionized water and thoroughly mixed to form a paste. The paste is then calcined at a temperature of from about 350° C. to about 450° C. to afford the desired mangesium:aluminum mixed metal oxide catalyst.

A preferred catalyst structure comprises a Group IIA and IIIA mixed metal oxide having a surface area of at least about 100 $m^2$/gm which may or may not be bonded to a support material. The decarboxylation catalysts on a support preferably have a surface area greater than about 20 $m^2$/gm to as high as about 260 $m^2$/gm, or greater depending upon which metal oxides are employed. In the case of magnesium:aluminum oxides, the surface area can be greater than about 50 $m^2$/gm to as high as about 260 $m^2$/gm, more preferably, greater than about 100 $m^2$/gm to as high as about 260 $m^2$/gm, determined according to the single point $N_2$ method.

The term "support," as used herein and in the claims, means a solid structure which does not adversely affect the catalytic properties of the catalyst and is at least as stable as the catalyst to the reaction medium. The support can function as a decarboxylation catalyst independent of the mixed metal oxide catalyst used herein, although it may have lower catalytic activity to the reaction. The support may act in concert with the catalyst to moderate the reaction. Some supports may contribute to the selectivity of the reaction. The catalyst structure can comprise from about 2 to about 60 percent by weight or greater of the support, more preferably from about 10 to about 50 percent by weight of the support, the remainder being the weight of the mixed metal oxides. Included in the weight of the support is the weight of any binding agent such as phosphates, sulfates, silicates, fluorides, and the like, and any other additive provided to stabilize or otherwise help in the manufacture of the catalyst. The support may be particles as large or larger than the catalyst component and "glued" to the decarboxylation catalyst by virtue of a binding medium.

The support may constitute a separate phase in the process of extruding the catalytic structure. In this embodiment, the support forming material, preferably as a paste is blended with a Paste of the decarboxylation catalyst or a partial condensate thereof. The paste may comprise the oxide forms of the support and the decarboxylation catalyst, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the mixed metal oxide decarboxylation catalyst.

A preferred group of mixed metal oxide catalysts for use in this invention include materials having the formula:

$$M_x^{2+} Q_y^{3+}(OH)_{2x+3y-nz} A_z^{n-} \cdot a\, H_2O \qquad (I)$$

wherein M is at least one divalent metal cation; Q is at least one trivalent metal cation; and A is at least one anion providing a valence (n−), wherein n is at least 1, e.g., between 1 and 4 and most often between 1 and 3, and wherein a is a positive number, M, Q, and A are provided in a proportion such that x/y is a number equal to or greater than 1, z has a value greater than zero and 2x+3y−nz is a positive number. M, Q and A may be selected to provide a layered structure. Preferably, x/y is in the range of 1 to 12, more preferably x/y is in the range of 1 to 6 and most preferably is in the range of 1 to 4. Preferably, z has a value such that x/z is between n and 12n, more preferably between n and 6n and most preferably between n and 4n.

Suitable divalent metal cations, M, broadly include elements selected from the Transition elements and Groups IIA and IVA of the Periodic Table as well as certain Group IIIB elements. As specific examples can be mentioned magnesium, calcium, titanium, vanadium, chromium, manganese, iron, cobalt, nickel, palladium, platinum, copper, zinc, cadmium, mercury, tin and lead. Divalent metal cations which are particularly suitable are magnesium, nickel, cobalt, zinc, calcium, strontium and copper. Suitable trivalent metal cations, Q, broadly include elements selected from the Transition elements and Groups IIIA and VA of the Periodic Table as well as certain Group IIIB elements. As specific examples can be mentioned aluminum, antimony, titanium, scandium, bismuth, vanadium, yttrium, chromium, iron, manganese, cobalt, ruthenium, nickel, gold, gallium, thallium, and cerium. Trivalent metal cations which are particularly suitable can be selected from aluminum, boron, gallium and lanthanum.

The composition of formula (I) also can include a wide range of anions, A. Any anion or combination of anions which can balance the charge of the cations can be used. Suitable anions include inter alia, halides (such as chloride, fluoride, bromide, and iodide), nitrite, nitrate, sulfite, sulfate, sulfonate, carbonate, chromate, cyanate, phosphite, phosphate, molybdocyanate, bicarbonate, hydroxide, arsenate, chlorate, ferrocyanide, borate, cyanide, cyanaurate, cyanaurite, ferricyanide, selenate, tellurate, bisulfate, as well as organic anions such as oxalate, acetate, hexanoate, sebacate, formate, benzoate, malonate, lactate, oleate, salicylate, stearate, citrate, tartrate, maleate, and the like. The class of metalate anions described in U.S. Pat. No. 4,667,045, including metavanadate, orthovanadate, molybdate, tungstate, hydrogen pyrovanadate and pyrovanadate, also are suitable as anion A. Anions suitable for use in combination with the metal cations previously identified as being particularly suitable are carbonate, halide, phosphate, chromate, sulfate, hydroxide, oxalate, acetate, nitrate, hexanoate, sebacate, vanadate, molybdate, tungstate and ferrocyanate.

The foregoing lists of suitable divalent and trivalent cations and suitable anions are meant to be illustrative and not exclusive. Those skilled in the art will recognize that other cations and anions can be used provided that the specific type of cations and their relative amounts (x/y ratio) and the specific type of anions and their relative amount result in a mixed metal oxide composition.

Included in the materials identified above are those based on exchangeable anionic clay minerals. For example, compositions of formula (I) wherein M is magnesium and Q is aluminum are related to hydrotalcites, while compositions in which M is nickel and A is aluminum are related to takovites. In fact, mixed metal oxides prepared using magnesium, nickel or cobalt as the divalent cation and aluminum as the trivalent cation exhibit the typical X-ray diffraction pattern of a hydrotalcite.

In another preferred aspect, the processes of this invention can utilize mixed metal oxide catalyst compositions prepared by calcining at an elevated temperature compositions according to formula (I). Suitable calcined compositions have the general formula:

$$M_x^{2+} Q_y^{3+} (O)_{(2x+3y-nz)/2} D_z^{n-} \qquad (II)$$

wherein M, Q, x, y, z and n have the same meanings defined above in connection with formula (I), and D is at least one nonvolatile anion. Nonvolatile anions may include, inter alia, halides, nitrates, Phosphites, phosphate, vanadate, molybdate, tungstate, sulfite, sulfate, chromate, arsenate, borate, chlorate and the like. This list is illustrative and not exclusive.

Heat treating the formula (I) compositions to prepare the calcined mixed metal oxide compositions of formula (II) can be done, for example, at a temperature in the range of 200° C. to 800° C. for a period of time of about 12 to 24 hours under an inert atmosphere such as nitrogen or in appropriate cases under an oxidizing atmosphere such as air.

Calcination of the mixed metal oxide composition dehydrates the composition and converts at least partially the metal hydroxides to metal oxides. Any nonvolatile anions may be present in the calcined material.

Provided the calcination temperature is not excessive, the mixed metal oxide can be rehydrated to the mixed metal hydroxide with water. Generally, the mixed metal oxide can be restored readily if the calcination temperature does not exceed about 600° C. Mixed metal oxides which are calcined under more severe conditions are not easily rehydrated and lower surface area materials are obtained.

Certain compositions falling within formula (I), such as hydrotalcite, which comprises a magnesium-aluminum hydroxide carbonate, and takovite, which comprises a nickel-aluminum hydroxide carbonate, are naturally occurring compositions. However, such compounds, as well as their related compositions, also can be prepared synthetically from inexpensive starting materials using well-known coprecipitation techniques. Procedures for direct synthesis of such materials are described in Itaya et al., *Inog. Chem.* (1987) 26:624–626; Taylor, R. M., *Clay Minerals* (1984) 19:591–603; Reichle, U.S. Pat. No. 4,476,324; Bish, D. L., *Bull. Mineral* (1980), 103:170–175 and Miyata et al., *Clays and Clay Minerals* (1977), 25:14–18. Using direct synthesis one has the ability to vary within wide limits the $M^{+2}/Q^{+3}$ atomic ratio as well as the anion.

For example, a composition of formula (I) where $M^{+2}$ is nickel or magnesium, $Q^{+3}$ is aluminum and $A^{n-}$ is carbonate can be prepared by adding, as aqueous solutions, (a) a mixture of nitrates, sulfates or chlorides of nickel or magnesium and aluminum in a desired atomic ratio of nickel or magnesium to aluminum, e.g. 6 atoms of nickel as nickel chloride to 2 atoms of aluminum as aluminum chloride, to (b) an aqueous solution of a stoichiometric amount of sodium hydroxide and a water soluble salt of the desired anion, e.g., sodium carbonate. The two solutions are mixed at a temperature of about 25° C. to 35° C. with vigorous stirring over a several-hour period to produce a slurry. The slurry then is heated for about 18 hours at a temperature within the range of about 50° C. to 200° C. (preferably between about 60° C. to 75° C.) in order to control crystallization and the ultimate particle size of the resulting crystals. After filtering, and thorough washing and drying, the solids are recovered, typically as a powder.

As noted above, this procedure can be adapted to a wide variety of cations, cation atomic ratios and anion substitutions. For example, water soluble salts of divalent magnesium, cobalt, zinc, copper, iron and calcium can be substituted for the nickel chloride illustrated above, while water soluble salts of trivalent gallium and lanthanum can replace the aluminum chloride. A wide variety of other combinations also will be apparent to those skilled in the art. Generally, the rate of metal ion addition to the aqueous caustic/anion solution is not critical and can be varied widely. For example, a preferred preparation method is described in Schaper, H. et al., *Applied Catalysis*, 54, 1989, 79-90, the disclosure of which is incorporated herein by reference. The reaction temperature also is not critical, although the temperature during the reaction preferably is kept below about 100° C. An important feature of the procedure is the use of efficient agitation during the mixing procedure to avoid the formation of undesired by-products.

Loading of an anion A or D into the mixed metal oxide compositions is influenced by a variety of factors including (i) the amount of anion used in the preparation relative to the metal cations, (ii) the atomic ratio of the metal cations (x/y) in the preparation procedure, (iii) the size of the cations and anions and (iv) the preparation procedure. As used herein, Θloading" is defined as the amount of available valences provided by a desired anion A or D expressed as a percentage of the total available valences for anion A or D. For example, carbonate loading in a hydrotalcite-type catalyst can be maximized by (i) using an excess (e.g., a greater than 3:1 molar ratio) of sodium carbonate to aluminum chloride during catalyst preparation and (2) adjusting the atomic ratio of magnesium to aluminum cations to about 2:1.

Mixed metal oxide compositions suitable as catalysts also can be prepared from the native or synthetic hydrotalcite-type compositions by ion exchange. For example, hydrotalcite can be treated at ambient conditions with 0.01N phosphoric acid for about 18 hours to replace the carbonate anion with Phosphate anion. A halide analog of hydrotalcite prepared directly or by anion exchange could be contacted with molybdic acid or a water soluble salt thereof, or with a water soluble salt of tungstic acid or vanadic acid in order to substitute the transition metal anion for the halide anion in the catalyst structure thereby to produce a mixed metal oxide composition of formula (I). Other ion exchanges will be apparent to those skilled in the art.

Calcined mixed metal oxide compositions may exhibit a higher level of selectivity/activity than uncalcined compositions. If a calcined mixed metal oxide catalyst composition experiences any decline in selectivity, it can be regenerated by a heat treatment in the presence of air to restore at least a portion of its initial level of selectivity/activity enhancement and reused. Conditions discussed above for calcining the hydrated mixed metal oxide compositions are suitable for regenerating compositions which have experienced a decline in activity.

Catalysts having the formulas (I) and (II) above wherein M is at least one of magnesium and calcium, Q is aluminum or gallium, A is at least one of carbonate, bicarbonate, phosphate, sulfate and nitrate, x/y is between 1 and 20, z has a value which satisfies the relationship: x/z is between n and 12n, and a is a positive number, are generally preferred for vapor phase decarboxylation due to their combination of activity (conversion of precursor) and selectivity. A preferred process involves a vapor phase process using mixed metal oxide catalyst wherein $M^{2+}$ is magnesium, $Q^{3+}$ is aluminum, $A^{n-}$ is carbonate, z/y is about 1, and z is about 1.

A group of preferred mixed metal oxide catalyst compositions which can be employed in the processes of this invention is disclosed in copending U.S. patent application Ser. No. 125,134, filed Nov. 25, 1987, (now abandoned in favor of continuation application U.S. Ser. No. 527,375, filed May 23, 1990) the disclosure of which is incorporated herein by reference.

The step (ii) decarboxylation reaction may be effected in the liquid or vapor or supercritical liquid states or mixtures thereof. In this context, the vapor phase reaction is intended to refer to the general vapor state of the starting materials. Though the step (ii) decarboxylation reaction conditions may range from subatmospheric or atmospheric to superatmospheric conditions, it is desirable to run the step (ii) reaction from about 1 mm Hg to about 5,000 mm Hg, preferably from about 100 mm Hg to about 2,500 mm Hg.

The temperature of the step (ii) decarboxylation reaction may be as low as about 150° C. to about 500° C. Preferably, the reaction temperature ranges from about 175° C. to about 375° C., and most preferably from about 225° C. to about 350° C.

Suitable carboxylated N,N,N-trisubstituted nitrogen-containing compounds for use in the step (ii) decarboxylation reaction can be prepared by the step (i) transesterification reaction or by other methods such as the carbonylation of N,N,N-trisubstituted nitrogen-containing compounds with carbon monoxide and oxygen at elevated temperatures in the presence of certain copper salts. Such a carbonylation process can be an alternative to the step (i) transesterification reaction and is encompassed within the generic scope of this invention. It is also appreciated that two or more $CO_2$ synthons can be reacted under conditions effective to produce a carboxylated N,N,N-trisubstituted nitrogen-containing compound.

The step (ii) decarboxylation reaction can be conducted in the presence of an inert diluent which can be either a liquid or gas. When a liquid diluent is employed, it should preferably be a good solvent for the starting materials, inert under the reaction conditions, and of such a nature that separation from the N,N,N-trisubstituted nitrogen-containing compound product will not be difficult. For instance, the boiling points of the diluent and the N,N,N-trisubstituted nitrogen-containing compound product should differ by an adequate amount and there should be no tendency of the diluent to form an azeotrope with the desired N,N,N-trisubstituted nitrogen-containing compound product.

Examples of useful liquid diluents that meet the foregoing qualifications include benzene, toluene, xylene, ethylbenzene, anisole, heptane, octane, nonane, decane, dibutyl ether, and the like. Hydrocarbons are preferred.

Illustrative gaseous diluents include for example, nitrogen, methane, hydrogen, carbon monoxide or carbon dioxide. The gaseous diluent should of course be chosen so that it does not prevent the preparation of the desired products.

While the use of such diluents may be beneficial, the processes of this invention can be operated using pure starting material(s) as a liquid or gaseous feed. The degree of dilution of the starting materials with various diluents may vary considerably depending upon any process constraints restricting the use of the diluent. For example, in commercial production, the use of very large quantities of some gaseous diluents may be disadvantageous due to the cost of pumping large volumes of the gaseous diluent and increased difficulty in isolating the product, which increase the energy costs of the process. With liquid diluents, the use of very large quantities may be disadvantageous due to the energy cost associated with large recovery and recycle. If the processes of this invention are to be carried out using a gaseous diluent, in general it is recommended that the starting material(s) constitute from about 1 to about 95, and preferably about 5 to about 50, mole percent of the starting material/carrier feed. Increasing the dilution of the starting material with a gaseous diluent such as hydrogen may tend to increase the selectivity of the reaction to the particular products desired. The amount of liquid diluent can vary widely, for instance, from no diluent to about 90 weight percent or greater of the total weight of the starting materials.

For processes of this invention in which a carboxylated N,N,N-trisubstituted nitrogen-containing compound is contacted with a mixed metal oxide catalyst under conditions effective to produce a N,N,N-tri- substituted nitrogen-containing compound or a N,N-disubstituted nitrogen-containing compound and a $CO_2$ synthon are contacted in the presence of a mixed metal oxide catalyst under conditions effective to produce a N,N,N-trisubstituted nitrogen-containing compound or other related processes described herein, it is understood that the process conditions described herein for the step (ii) decarboxylation reaction can desirably be employed for such processes.

The processes of this invention are useful for preparing N,N,N-trisubstituted nitrogen-containing compounds such as those embraced by the formulae $RN(R_1)R$ or $RN(R_2)R$ wherein R, $R_1$ and $R_2$ are as defined above. It is understood that the R substituents together, the R and $R_1$ substituents together, and the R and $R_2$ substituents together can complete a heterocycloalkyl ring which can be substituted or unsubstituted. Illustrative N,N,N-trisubstituted nitrogen-containing compounds prepared by the processes of this invention include, for example, N-methyldiethanolamine, 1-methylpiperazine, 1,4-dimethylpiperazine, 1-ethylpiperazine, 1,4-diethylpiperazine, 1-hydroxyethylpiperazine, 1,4-dihydroxyethylpiperazine, 2-piperazinoethyl 2-methoxyethyl ether, 1-aminoethylpiperazine, 1,4-diaminoethylpiperazine, N-aminoethylmorpholine, N-methylmorpholine, N-ethylmorpholine, N-hydroxyethylmorpholine, N,N-disubstituted poly(oxyalkylene) derivatives such as amine-terminated polyethers, N,N'-dimethylethyleneurea, N-methyl-2-oxazolidinone, N-(2-hydroxyethyl)ethyleneurea, 2-(N,N-dimethylamino)ethyl 2-methoxyethyl ether and the like.

Illustrative of suitable N,N,N-trisubstituted nitrogen-containing compounds which can be prepared by the processes of this invention include those permissible N,N,N-trisubstituted nitrogen-containing compounds, including any permissible derivatives of described N,N,N-trisubstituted nitrogen-containing compounds, which are described in Kirk-Othmer, Encyclopedia of Chemical Technology, Third Edition, 1984, the pertinent portions of which are incorporated herein by reference.

The N,N,N-trisubstituted nitrogen-containing compound products produced by the processes of this invention can be separated by distillation. For example, a crude reaction product can be subjected to a distillation-separation at atmospheric or reduced pressure through a packed distillation column. Reactive distillation may be useful in conducting the step (i) transesterification reaction.

The processes of this invention may be carried out using, for example, a fixed bed reactor, a fluid bed reactor, or a slurry reactor. The optimum size and shape of the catalyst will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the decarboxylation catalyst. When complete conversion is not desired or not obtainable, the starting materials can be separated from the N,N,N-trisubstituted nitrogen-containing compound product, for example by distillation, and the starting materials then recycled back into the reaction zone.

The processes are conducted for a period of time sufficient to produce the N,N,N-trisubstituted nitrogen-containing compound products. The exact reaction time employed is dependent, in part, upon factors such as temperature, nature and proportion of starting materials, and the like. The reaction time will normally be within the range of from about one-half to about 100 hours or more, and preferably from less than about one to about ten hours.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Illustrative of suitable reactants in effecting the processes of this invention include by way of example:
OX—2-oxazolidinone
EU—ethylene urea
PIP—piperazine
EC—ethylene carbonate
PC—propylene carbonate
DMC—dimethyl carbonate
MEDC—2-(2-methoxyethoxy)ethyl N,N-dimethyl carbamate
MO—morpholine
TMU—N,N,N',N'-tetramethyl urea
DEC—diethyl carbonate
MEMC—2-(2-methoxyethoxy)ethyl methyl carbamate
DEA—diethanolamine
MCC—methyl chlorocarbonate
MDEAC—methyl diethanolamine carbamate
MPC—methyl 1-piperazine carboxylate
EPC—ethyl 1-piperazine carboxylate
MOXC—methyl 2-oxazolidinone carboxylate
MIZC—methyl 2-imidazolidinone carboxylate
MMC—methyl 1-morpholine carboxylate Illustrative of suitable products prepared by the processes of this invention include by way of example:
AEP—1-aminoethylpiperazine DAEP—1,4-diaminoethylpiperazine
AEM - aminoethylmorpholine
DMP—1,4-dimethylpiperazine
MP—1-methylpiperazine
MDEA—N-methyldiethanolamine
ATP—amine-terminated poly(oxyalkylene) derivatives
DMME—2-(N,N-dimethylamino)ethyl 2-methoxyethyl ether
DMEU—N,N'-dimethylethyleneurea
HEP—1-hydroxyethylpiperazine
HPM—1-(2-hydroxypropyl)morpholine
DHEP—1,4-dihydroxyethylpiperazine
AEM—N-aminoethylmorpholine
MM—N-methylmorpholine
EM—N-ethylmorpholine
HEM—N-hydroxyethylmorpholine
PME—2-piperazinoethyl 2-methoxyethyl ether
EP—1-ethylpiperazine
DEP—1,4-diethylpiperazine
MOX—N-methyl-2-oxazolidinone
HPP—1-(2-hydroxypropyl)piperazine
DHPP—1,4-(2-hydroxypropyl)piperazine
HEEU—N-(2-hydroxyethyl)ethyleneurea Illustrative of permissible reactions encompassed within the scope of this invention include, for example, the following reactant/product combinations:

| REACTANT(S) | PRODUCT(S) |
|---|---|
| OX, PIP | AEP, DAEP |
| OX, MO | AEM |
| PIP, DMC | DMP, MP |
| DEA, DMC | MDEA |
| PIP, EC | HEP, DHEP |
| MO, EC | HEM |
| PIP, MEMC | PME |
| PIP, DEC | EP, DEP |
| OX, DMC | MOX |
| EU, DMC | DMEU |
| MEDC | DMME |
| MO, PC | HPM |
| PIP, PC | HPP, DHPP |

As used herein, the phrase "residue of an organic compound" is contemplated to include all permissible residues of organic compounds. In a broad aspect, the permissible residues include acyclic and cyclic, branched and unbranched, carbocyclic and heterocyclic, aromatic and nonaromatic residues of organic compounds. Illustrative organic compound residues include, for example, alkyl, aryl, cycloalkyl, heterocycloalkyl, alkyl(oxyalkylene), aryl(oxyalkylene), cycloalkyl(oxyalkylene), heterocycloalkyl(oxyalkylene), hydroxyalkyl, hydroxyalkyl(oxyalkylene), hydroxy(alkyleneoxy) and the like. The permissible residues can be substituted or unsubstituted and the same or different for appropriate organic compounds. This invention is not intended to be limited in any manner by the permissible residues of organic compounds.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate the processes of this invention.

The following apparatus was used for the preparation of N,N,N-trisubstituted nitrogen-containing compounds in the examples. An Applied Test Systems, Inc. Model 3620 Split Test Oven equipped with a preheater (stainless steel 1/8 inch o.d. ×2 feet) and ¼ inch (o.d.) stainless steel reactor tube (8 inch length) was packed with catalyst and heated to the desired reaction temperature using a Honeywell Dial-A-Trol temperature controller. The temperatures at the top of the reactor and the bottom were monitored using a digital temperature readout. The liquid feed was added (downflow) to the reactor via a Fluid Metering Inc. RP-G20 drive pump equipped with an ¼ inch pump head. The system was maintained under nitrogen, which was introduced prior to the liquid Preheater and was monitored with a rotometer. The product mixture was collected in a 100 milliliter round bottom flask, vented first to a dry ice-/acetone trap and then a Firestone valve. Analysis was performed by capillary gas chromatography (FID) using a DB-1701 column.

EXAMPLE 1

Preparation of Decarboxylation Catalyst

A total of 44.1 grams of magnes hexahydrate and 66.0 grams of aluminum nitrate nonahydrate were dissolved in 200 milliliters of distilled water to give a first solution. A total of 4.8 grams of ammonium carbonate was dissolved in 200 milliliters of concentrated ammonium hydroxide (28-29 weight percent) to give a second solution. About 100 milliliters of distilled water was heated in a flask at a temperature of 40° C. and the first and second solutions were combined simultaneously with good agitation using a mechanical stirrer. The rates of addition of the first and second solutions were adjusted to maintain a pH of 9-10. The total addition took 10 minutes and a final pH of 9.5 was obtained. The contents were stirred at a temperature of 40° C. for a period of 40 minutes. The resulting precipitate was filtered and washed (ca. 300 milliliters three to four times) with water at a temperature of 60° C. until the pH of the wash was neutral. The filter cake was dried at a temperature of 80° C. overnight. The weight of the dried filter cake was about 16 grams. The filter cake was then calcined in air at a temperature of 400° C. for a period of 3 hours to afford a magnesium:aluminum mixed metal oxide.

EXAMPLE 2

Preparation of 1-Methuloioerazine and 1,4-Dimethylpiperazine

Using the apparatus described hereinabove, a solution containing 1.72 grams (0.02 mol) of piperazine and 7.21 grams (0.08 mol) of dimethyl carbonate in 20 milliliters of methanol was passed through a catalyst bed containing 2.0 grams of a magnesium:aluminum mixed metal oxide (3/16 inch tablets, Mg/Al 3:1) at a temperature of 250° C. and a flow rate of about 0.3 milliliters per minute. After a period of 1 hour, the reaction was stopped and the product analyzed. The results are given in Table I below.

TABLE I

| Product Composition, area %: | |
|---|---|
| Dimethyl carbonate | 13.75 |
| 1,4-Dimethylpiperazine | 34.27 |
| 1-Methylpiperazine | 37.57 |
| Piperazine | 9.01 |
| Methyl 4-methyl-1-piperazine carboxylate | 0.40 |
| Methyl 1-piperazine carboxylate | 1.01 |

EXAMPLE 3

Preparation of 1-Ethylpiperazine and 1,4-Diethylpiperazine

Using the apparatus described hereinabove, a 30 weight percent solution of ethyl 1-piperazinecarboxylate in cyclohexane was passed through a catalyst bed containing 6.0 grams of a magnesium:aluminum mixed metal oxide (⅛ inch tablets, Mg/Al 3:1) at a temperature of 325° C. and a liquid feed rate of 0.32 milliliters per minute. After a period of 0.5 hours, the cyclohexane was removed under vacuum and the product mixture (liquid and solid) was dissolved in water. The results are given in Table II below.

TABLE II

| Product Composition, area %: | |
|---|---|
| Ethanol | 0.7 |
| 1,4-Diethylpiperazine | 17.4 |
| 1-Ethylpiperazine | 63.9 |
| Piperazine | 14.2 |
| Others | 3.7 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

I claim:

1. A process for preparing N,N,N-trisubstituted acyclic or nonaromatic cyclic nitrogen-containing compounds which comprises contacting a carboxylated N,N,N-trisubstituted acyclic or nonaromatic cyclic nitrogen-containing compound with a mixed metal oxide catalyst under decarboxylation conditions effective to produce the N,N,N-trisubstituted acyclic or nonaromatic cyclic nitrogen-containing compound.

2. The process of claim 1 wherein the mixed metal oxide catalyst has a surface area greater than about 50 m²/gm.

3. The process of claim 1 wherein the carboxylated N,N,N-trisubstituted nitrogen-containing compound comprises methyl diethanolamine carbamate, methyl 1-piperazine carboxylate, methyl 2-oxazolidinone carboxylate, methyl 2-imidazolidinone carboxylate, methyl 1-morpholine carboxylate, 2(2-methoxyethoxy)ethyl methyl carbamate, ethyl 1-piperazine carboxylate, methyl 4-methyl-1-piperazine carboxylate, 2-(2-methoxyethoxy)ethyl N,N-dimethyl carbamate, ethyl 2-oxazolidinone carboxylate, ethyl 2-imidazolidinone carboxylate or ethyl 1-morpholine carboxylate.

4. The process of claim 1 wherein the mixed metal oxide catalyst comprises two or more metal oxides selected form the group consisting of Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides and Group VIA metal oxides.

5. The process of claim 4 wherein the mixed metal oxide catalyst comprises two or more oxides selected form the group consisting of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

6. The process of claim 1 wherein the mixed metal oxide catalyst comprises at least one group IIA metal oxide.

7. The process of claim 1 wherein the mixed metal oxide catalyst comprises a Group IIA metal oxide and a group IIIA metal oxide.

8. The process of claim 1 wherein the mixed metal oxide catalyst comprises a Group IIA metal oxide and a Group IIIB metal oxide.

9. The process of claim 1 wherein the mixed metal oxide catalyst comprises magnesium oxide and aluminum oxide.

10. The process of claim 1 wherein the mixed metal oxide catalyst comprises a high surface area mixed metal oxide.

11. The process of claim 6 wherein the Group IIA metal oxide comprises from about 10 weight percent to about 90 weight percent of the weight of the catalyst.

12. The process of claim 1 wherein the mixed metal oxide catalyst is associated with a support material.

13. The process of claim 12 wherein the support comprises an alumina material or an alumina-silica material.

14. The process of claim 12 wherein the support comprises a silica material or a silica-alumina material.

15. The process of claim 12 wherein the support comprises from about 2 to about 50 percent by weight of the mixed metal oxide catalyst.

16. The process of claim 1 wherein the mixed metal oxide catalyst comprises:

(a) a material having the formula

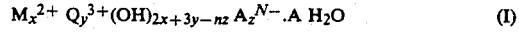

$$M_x^{2+} Q_y^{3+}(OH)_{2x+3y-nz} A_z^{N-} \cdot A\ H_2O \qquad (I)$$

wherein M is at least one divalent metal cation; Q is at least one trivalent metal cation; and A is at least one anion providing a valence (n−), wherein n is 1 to 4 and wherein a is a positive number, M, Q and A are provided in a proportion such that x/y is a number equal to or greater than 1, z has a value greater than zero and 2x+3y−nz is a positive number, or (b) a material prepared by calcining the material of formula (I) having the formula

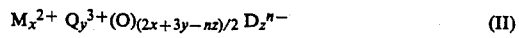

$$M_x^{2+} Q_y^{3+}(O)_{(2x+3y-nz)/2} D_z^{n-} \qquad (II)$$

wherein M, Q, x, y, z and n have the same meanings defined above in connection with formula (I), and D is at least one nonvolatile anion.

17. The process of claim 16 wherein x/y is a number between 1 and 12 and z has a value which satisfies the relationship: x/z is between n and 12n.

18. The process of claim 16 wherein A is selected form the group consisting of carbonate, halide, phosphite, phosphate, chromate, sulfate, hydroxide, oxalate, acetate, nitrate, hexanoate, sebacate, vanadate, molybdate, tungstate and ferrocyanate.

19. The process of claim 16 wherein D is selected form the group consisting of halides, phosphite, phosphate, vanadate, molybdate, tungstate, sulfite, sulfate, chromate, arsenate, borate and chlorate.

20. The process of claim 16 wherein x/y is a number between 1 and 6 and z has a value which satisfies the relationship: x/z is between n and 6n.

21. The process of claim 16 wherein said material prepared by calcining the material of formula (I) has been heat treated at a temperature in the range of 200° C. to 800° C. for 12 to 24 hours.

22. The process of claim 16 wherein M is magnesium and and Q is aluminum.

23. A process for preparing N,N,N-trisubstituted nitrogen-containing compounds which comprises contact a carboxylated N,N,N-trisubstituted nitrogen-containing compound with a mixed metal oxide catalyst under conditions effective to produce the N,N,N-trisubstituted nitrogen-containing compound, wherein the N,N,N-trisubstituted nitrogen-containing compound is selected from the group consisting of N-methyldiethanolamine, 1-methylpiperazine, N-methyl-2-oxazolidinone, N,N'-dimethylethyleneurea, N-(2-hydroxyethyl)ethyleneurea, N-methylmorpholine, 2-(N,N-dimethylamino)ethyl 2-methoxyethyl ether, N-aminoethylmorpholine, 1,4-diaminoethylpiperazine, N-hydroxyethylmorpholine, 1,4- dihydroxyethylpiperazine, 1,4-dimethylpiperazine, 1-hydroxyethylpiperazine, 2-piperazinoethyl 2-methoxyethyl ether, 1-aminoethylpiperazine, N-ethylmorpholine, an amine terminated polyether, 1-ethylpiperazine and 1,4-diethylpiperazine.

24. The process of claim 1 wherein the N,N,N-trisubstituted nitrogen-containing compound comprises a N-substituted piperazine, a N,N'-disubstituted piperazine, a N-substituted morpholine, a N-substituted 2-imidazolidinone, a N,N'-disubstituted 2-imidazolidinone or a N-substituted 2-oxazolidinone.

25. A process for preparing N,N,N-trisubstituted acyclic or nonaromatic cyclic nitrogen-containing compounds which comprises (i) contacting a N,N-disubstituted acyclic or nonaromatic cyclic nitrogen-containing compound with a CO2 synthon under transesterification conditions effective to produce a carboxylated N,N,N-trisubstituted acyclic or nonaromatic cyclic nitrogen-containing compound, and (ii) contacting the carboxylated N,N,N-trisubstituted acyclic or nonaromatic cyclic nitrogen-containing compound with a mixed metal oxide catalyst under decarboxylation conditions effective to product the N,N,N-trisubstituted acyclic or nonaromatic cyclic nitrogen-containing compound.

26. The process of claim 25 wherein the N,N-disubstituted nitrogen-containing compound comprises piperazine, morpholine, diethanolamine, 2-oxazolidinone, 2-imidazolidinone, piperidine, pyrrolidine, diisopropylamine, dimethylamine or diethylamine.

27. The process of claim 25 wherein the CO2 synthon is selected from the group consisting of ethylene carbonate, dimethyl carbonate, diethyl carbonate, 2-oxazolidinone, propylene carbonate, methyl chlorocarbonate and N,N,N', N'-tetramethylurea.

28. The process of claim 25 wherein the CO2 synthon comprises ethylene carbonate in association with monoethanolamine.

29. The process of claim 25 wherein the carboxylated N,N,N-trisubstituted nitrogen-containing compound comprises methyl diethanolamine carbamate, methyl 1-piperazine carboxylate, methyl 2-oxazolidinone carboxylate, methyl 2-imidazolidinone carboxylate, methyl 1-morpholine carboxylate, 2-(2-methoxyethoxy)ethyl methyl carbamate, ethyl 1-piperazine carboxylate, methyl 4-methyl-1-piperazine carboxylate, 2-(2-methoxyethoxy)ethyl N,N-dimethyl carbamate, ethyl 2-oxazolidinone carboxylate, ethyl 2-imidazolidinone carboxylate or ethyl 1-morpholine carboxylate.

30. The process of claim 25 wherein the mixed metal oxide catalyst comprises two or more metal oxides selected from the group consisting of Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides and Group VIA metal oxides.

31. The process of claim 30 wherein the mixed metal oxide catalyst comprises two or more oxides selected from the group consisting of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

32. The process of claim 25 wherein the mixed metal oxide catalyst comprises at least one Group IIA metal oxide.

33. The process of claim 25 wherein the mixed metal oxide catalyst comprises a Group IIA metal oxide and a Group IIIA metal oxide.

34. The process of claim 25 wherein the mixed metal oxide catalyst comprises a Group IIA metal oxide and a Group IIIB metal oxide.

35. The process of claim 25 wherein the mixed metal oxide catalyst comprises magnesium oxide and aluminum oxide.

36. The process of claim 25 wherein the N,N,N-trisubstituted nitrogen-containing compound comprises N-methyldiethanolamine, 1-methylpiperazine, N-methyl-2-oxazolidinone, N,N'-dimethylethyleneurea, N-(2-hydroxyethyl)ethyleneurea, N-methylmorpholine, 2-(N,N-dimethylamino ethyl 2-methoxyethyl ether, N-aminoethylmorpholine, 1,4-diaminoethylpiperazine, N-hydroxyethylmorpholine, 1,4-dihydroxyethylpiperazine, 1,4-dimethylpiperazine, 1-hydroxyethylpiperazine, 2-piperazinoethyl 2-methoxyethyl ether, 1-aminoethylpiperazine, N-ethylmorpholine, an amine terminated polyether, 1-ethylpiperazine or 1,4-diethylpiperazine.

37. The process of claim 25 wherein the N,N,N-trisubstituted nitrogen-containing compound comprises a N-substituted piperazine, a N,N'-disubstituted Piperazine, a N-substituted morpholine, a N-substituted 2-imidazolidinone, a N,N'-disubstituted 2-imidazolidinone or a N-substituted 2-oxazolidinone.

38. A process for preparing N,N,N-trisubstituted acyclic or nonaromatic cyclic nitrogen-containing compounds which comprises contacting a N,N-disubstituted acyclic or nonaromatic cyclic nitrogen-containing compound with a CO2 synthon in the presence of a mixed metal oxide catalyst under decarboxylation conditions effective to produce the N,N,N-tri-substituted acyclic or nonaromatic cyclic nitrogen-containing compound.

39. The process of claim 38 wherein the N,N-disubstituted nitrogen-containing compound comprises piperazine, morpholine, diethanolamine, 2-oxazolidinone, 2-imidazolidinone, piperidine, pyrrolidine, diisopropylamine, dimethylamine or diethylamine.

40. The process of claim 38 wherein the $CO_2$ synthon comprises a substituted or unsubstituted carbonate, chlorocarbonate, carbonate acid, carbamate, carbamic acid, oxalate, 2-oxazolidinone, urea, ester, phosgene, chloroformates, carbon dioxide, orthocarboxylate, sulfurous acid or sulfurous acid ester.

41. The process of claim 38 wherein the $CO_2$ synthon comprises ethylene carbonate, dimethyl carbonate, diethyl carbonate, 2-oxazolidinone, propylene carbonate, methyl chlorocarbonate or N,N,N',N'-tetramethylurea.

42. The process of claim 38 wherein the $CO_2$ synthon comprises ethylene carbonate in association with monoethanolamine.

43. The process or claim 38 wherein the mixed metal oxide catalyst comprises two or more mixed oxides selected form the group consisting of Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides and Group VIA metal oxides.

44. The process of claim 43 wherein the mixed metal oxide catalyst comprises two or more oxides selected from the group consisting of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

45. The process of claim 38 wherein the mixed metal oxide catalyst comprises at least one Group IIA metal oxide.

46. The process of claim 38 wherein the mixed metal oxide catalyst comprises a Group IIA metal oxide and a Group IIIA metal oxide.

47. The process of claim 38 wherein the mixed metal oxide catalyst comprises a Group IIA metal oxide and a Group IIIB metal oxide.

48. The process of claim 38 wherein the mixed metal oxide catalyst comprises magnesium oxide and aluminum oxide.

49. The process of claim 38 wherein the N,N,N-trisubstituted nitrogen-containing compound comprises N-methyldiethanolamine, 1-methylpiperazine, N-methyl-2-oxazolidinone, N,N'-dimethylethyleneurea, N-(2-hydroxyethyl)ethyleneurea, N-methylmorpholine, 2-(N,N-dimethylamino)ethyl 2-methoxyethyl ether, N-aminoethylmorpholine, 1,4-diaminoethylpiperazine, N-hydroxyethylmorpholine, 1,4-dihydroxyethylpiperazine, 1,4-dimethylpiperazine, 1-hydroxyethylpiperazine, 2-piperazinoethyl 2-methoxyethyl ether, 1-aminoethylpiperazine, N-ethylmorpholine, an amine-terminated polyether, 1-ethylpiperazine or 1,4-diethylpiperazine.

50. The process of claim 38 wherein the N,N,N-trisubstituted nitrogen-containing compound comprises a N-substituted piperazine, a N,N'-disubstituted piperazine, a N-substituted morpholine, a N-substituted 2-imidazolidinone, a N,N'-disubstituted 2-imidazolidinone or a N-substituted 2-oxazolidinone.

* * * * *